United States Patent
Lempka et al.

(10) Patent No.: US 9,463,327 B2
(45) Date of Patent: Oct. 11, 2016

(54) SYSTEMS AND METHODS FOR DETERMINING EFFECTIVE STIMULATION PARAMETERS

(71) Applicant: THE CLEVELAND CLINIC FOUNDATION, Cleveland, OH (US)

(72) Inventors: Scott Lempka, Cleveland Heights, OH (US); Andre G. Machado, Beachwood, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

(21) Appl. No.: 14/726,702

(22) Filed: Jun. 1, 2015

(65) Prior Publication Data

US 2015/0360039 A1    Dec. 17, 2015

Related U.S. Application Data

(60) Provisional application No. 62/013,014, filed on Jun. 17, 2014.

(51) Int. Cl.

| | |
|---|---|
| *A61N 1/00* | (2006.01) |
| *A61N 1/372* | (2006.01) |
| *A61B 6/00* | (2006.01) |
| *A61N 1/36* | (2006.01) |
| *A61N 1/362* | (2006.01) |
| *G06F 19/00* | (2011.01) |
| *A61B 6/03* | (2006.01) |

(52) U.S. Cl.
CPC ....... *A61N 1/37264* (2013.01); *A61N 1/36139* (2013.01); *A61B 6/032* (2013.01); *A61B 6/037* (2013.01); *A61B 6/5217* (2013.01); *A61N 1/362* (2013.01); *A61N 1/36003* (2013.01); *G06F 19/3431* (2013.01); *G06F 19/3443* (2013.01)

(58) Field of Classification Search
CPC ........... A61B 6/5217; A61N 1/36003; A61N 1/36139; A61N 1/362; A61N 1/37264; G06F 19/3431; G06F 19/3443
See application file for complete search history.

(56) References Cited

U.S. PATENT DOCUMENTS

| | | | |
|---|---|---|---|
| 8,160,328 B2* | 4/2012 | Goetz et al. | 382/128 |
| 8,315,689 B2 | 11/2012 | Jenkins et al. | |
| 2006/0217781 A1 | 9/2006 | John | |
| 2011/0208264 A1 | 8/2011 | Gliner et al. | |
| 2011/0270348 A1 | 11/2011 | Goetz | |
| 2014/0039312 A1 | 2/2014 | Rockweiller et al. | |

FOREIGN PATENT DOCUMENTS

| | | |
|---|---|---|
| EP | 2719427 A1 | 4/2014 |
| WO | 2006017053 A1 | 2/2006 |
| WO | 2007084456 A2 | 7/2007 |

OTHER PUBLICATIONS

PCT International Search Report and Written Opinion for PCT/US2015/033466, mailed Feb. 15, 2016, pp. 1-14.

* cited by examiner

*Primary Examiner* — George Manuel
(74) *Attorney, Agent, or Firm* — Tarolli, Sundheim, Covell & Tummino LLP (57) ABSTRACT

One aspect of the present disclosure relates a method for determining effective stimulation parameters to apply to a patient in order to improve the patient's medical condition. The method can employ functional and/or structural imaging to determine the effective stimulation parameters. As such, the method includes programming a stimulation device with an initial stimulation parameter. An image can be received of at least a portion of the patient that is affected by a stimulation by the stimulation device. Based on the image, the efficacy of the stimulation with the at least one initial stimulation parameter can be assessed. The at least one initial stimulation parameter can be updated based on the assessed efficacy.

19 Claims, 10 Drawing Sheets

SYSTEMS AND METHODS FOR DETERMINING EFFECTIVE STIMULATION PARAMETERS

RELATED APPLICATIONS

This application claims the benefit of U.S. Provisional Application No. 62/013,014, filed Jun. 17, 2014, entitled "METHODS FOR DETERMINING EFFECTIVE NEUROSTIMULATION PARAMETERS." This provisional application is hereby incorporated by reference in its entirety for all purposes.

TECHNICAL FIELD

The present disclosure relates generally to systems and methods for determining at least one effective stimulation parameter based on feedback from an image of a patient.

BACKGROUND

Spinal cord stimulation (SCS) for chronic pain management is safe and widely utilized throughout the world. It represents one of the most common neurostimulation therapies, not just for chronic pain management, but for many other indications. In the United States, it represents a market size of more than a billion dollars per year. Traditionally, SCS has been programmed based on patient-reported paresthesias, i.e., tingling sensations, induced by the electrical stimulation. Clinical observations suggest that successful pain relief with SCS requires that these paresthesias are generated over the painful areas. However, with this programming method, only approximately 50% of patients obtain sufficient pain relief. This success rate means that SCS fails in half of patients. Because SCS is typically considered a treatment for patients with refractory pain, these patients have few, if any, other options. It is also not clear if these paresthesias are necessary for pain relief or if they are just epiphenomena. Further, the most common outcome measure for pain therapies is pain ratings provided by the patient on a 0-10 or 0-100 point scale, which is a very subjective method to evaluate the clinical success of the treatment.

Another form of neurostimulation, deep brain stimulation (DBS), has been evaluated for different indications such as depression, Alzheimer's disease, Parkinson's disease, and essential tremor. Unlike programming DBS for essential tremor, where the effects of a given stimulation setting on the disease can be immediately observed (e.g., reduction in tremor), it can be much harder to program DBS for other indications, particularly when it may take several days or weeks for a given stimulation setting to produce the desired effect.

The traditional programming strategies employed with SCS and DBS each suffer from various limitations. As such, there is a need for better and more objective strategies for determining effective neurostimulation parameters for different disease states.

SUMMARY

The present disclosure relates generally to systems and methods for determining effective parameters for stimulation based on feedback from an image of a patient. For example, a structural image and/or a functional image can be input as feedback so that a new, more effective parameter for the stimulation can be determined.

According to an aspect, the present disclosure provides a method for determining effective parameters for stimulation. The method can be executed by a system comprising a processor. A stimulation device can be programmed with at least one initial stimulation parameter. An image of at least a portion of the patient can be received after implantation of the stimulation device programmed with the at least one initial stimulation parameter. The at least the portion of the patient is affected by a stimulation by the stimulation device. An efficacy of the stimulation can be assessed with the at least one initial stimulation parameter based on the image. Based on the assessed efficacy, a new, more effective parameter for the stimulation can be determined.

According to another aspect, the present disclosure provides a system that can be used to determine effective parameters for stimulation. The system can include a memory storing computer-executable instructions and a processor to access the memory and execute the computer-executable instructions to at least: program a stimulation device implanted in a patient with an initial stimulation parameter; receive an image of at least a portion of the patient, wherein the at least the portion of the patient is affected by a stimulation by the stimulation device; and assess an efficacy of the stimulation with the at least one theoretically optimal stimulation parameter based on the functional image. Based on the assessed efficacy, a new, more effective parameter for the stimulation can be determined.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

In addition, it will be understood that when an element is referred to as being "on," "attached" to, "connected" to, "coupled" with, "contacting," in "communication" with etc., another element, it can be directly on, attached to, connected to, coupled with, contacting, or in communication with the other element or intervening elements may also be present. In contrast, when an element is referred to as being, for example, "directly on," "directly attached" to, "directly connected" to, "directly coupled" with, "directly contacting," or in "direct communication" with another element, there are no intervening elements present.

It will also be appreciated by those of skill in the art that references to an element that is disposed "adjacent" another element may have portions that overlap or underlie the adjacent element.

As used herein, the terms "stimulation," "stimulated," "activation," and "activated" refer to any artificial input that causes one or more neuromodulatory effects (e.g., excitation/activation, inhibition, conduction block, modulation of response to other inputs, or the like) in at least a portion of neurons in a target tissue. The stimulation can be electrical stimulation, magnetic stimulation, optical stimulation, thermal stimulation, electromagnetic stimulation, or the like. In some instances, the target tissue can be neural tissue, such as a portion of the brain, the spinal cord, the peripheral nervous system. In other instances, the target tissue can be another electrically conductive tissue, such as cardiac tissue, muscle tissue, or the like. Accordingly, the stimulation can be used for deep brain stimulation, cortical stimulation, spinal cord stimulation, peripheral nerve stimulation, muscular stimulation, cardiac stimulation, or the like. Indeed, any type of neuromodulatory or neuroaugmentatory procedure or method is covered within the definition of "stimulation".

As used herein, the term "neuromodulation" refers to the specific case of stimulation that involves activation or inhibition of neuronal conduction in at least a portion of neurons in a target tissue.

As used herein, the terms "parameter for stimulation" and "stimulus parameter" refer to a measure that can be one of a set of parameters that define the stimulation. In some instances, the parameters for stimulation can include amplitude, a frequency, a pulse width, a duration, and the like. In other instances, the parameters for stimulation can include a location of a contact (e.g., a moveable contact), a stimulation configuration (e.g., which contact is selected to apply the stimulation and to what intensities, timing, etc.).

As used herein, the term "patient-specific computer model" refers to a computer model of a human physiology and/or pathophysiology that are individualized to patient-specific data and possesses predictive qualities.

As used herein, the term "imaging" can refer to a technique of creating a visual representation of the interior of a body for clinical analysis. Examples of medical imaging can include structural imaging and functional imaging. Structural imaging can reveal the underlying structure of at least a portion of the body. Functional imaging can provide direct or indirect measurements of physiological activity (e.g., neural activity). Examples of functional imaging modalities can include functional magnetic resonance imaging (fMRI), evoked potentials, local field potential (LFP), electrocorticography (ECoG), electroencephalography (EEG), magnetoencephalography (MEG), electromyography (EMG), positron emission tomography (PET), magnetic resonance spectroscopy (MRS), single-photon emission computed tomography (SPECT), near-infrared (NIR) spectroscopy, optical tomography (OT), ultrasound, laser Doppler measurements, and the like.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc.

As used herein, the terms "optimal" and "sub-optimal" can be measures of clinical efficacy. For example, when a stimulation is deemed optimal, it can refer to a stimulation parameter being used that produces a stimulation with a clinically relevant outcome. When a stimulation is deemed sub-optimal, it can refer to a stimulation parameter being used that produces a stimulation with an outcome above/below clinical relevance. For example, in some instances, a sub-optimal stimulation is 10% or more different than a clinically relevant stimulation. In some instances, a sub-optimal stimulation is 5% or more different than a clinically relevant stimulation.

II. Overview

The present disclosure relates generally to systems and methods for determining at least one effective stimulation parameter based on structural and/or functional imaging. In some instances, an image can provide feedback about the effectiveness of a stimulation parameter. Based on the feedback, the stimulation parameter can be updated.

The systems and methods of the present disclosure can be used to guide and determine effective parameters in a patient suffering from a medical condition in need of treatment. Notably, the parameters can be determined on an objective manner by the systems and methods described herein. As such, the systems and methods described herein address the problems with therapies guided by simplistic or subjective measurements by providing surrogate or biomarker objective measurements of a patient's condition (e.g., the activity of multiple brain networks). Advantageously, the systems and methods described herein can be performed while a patient is awake or under sedation/anesthesia which is beneficial to a large number of patients in which programming is conducted awake, but also is viable for patients undergoing procedures under sedation or anesthesia.

III. Systems

One aspect of the present disclosure can include a system that can determine the efficacy of at least one stimulation parameter based on a structural image and/or a functional image. The systems as illustrated in FIGS. 1-7 can be implemented on/by one or more computing devices that can include a memory storing computer-executable instructions for implementing the systems and a processor to access the memory and execute the computer-executable instructions to perform operations of the systems. In some instances, the computing device can be, for example, a general purpose computer, special purpose computer, and/or other programmable data processing apparatus. Accordingly, the computer-readable medium can be any non-transitory medium that is not a transitory signal and can contain or store the program for use by or in connection with the instruction or execution of a system, apparatus, or device. The computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

Figure 1:
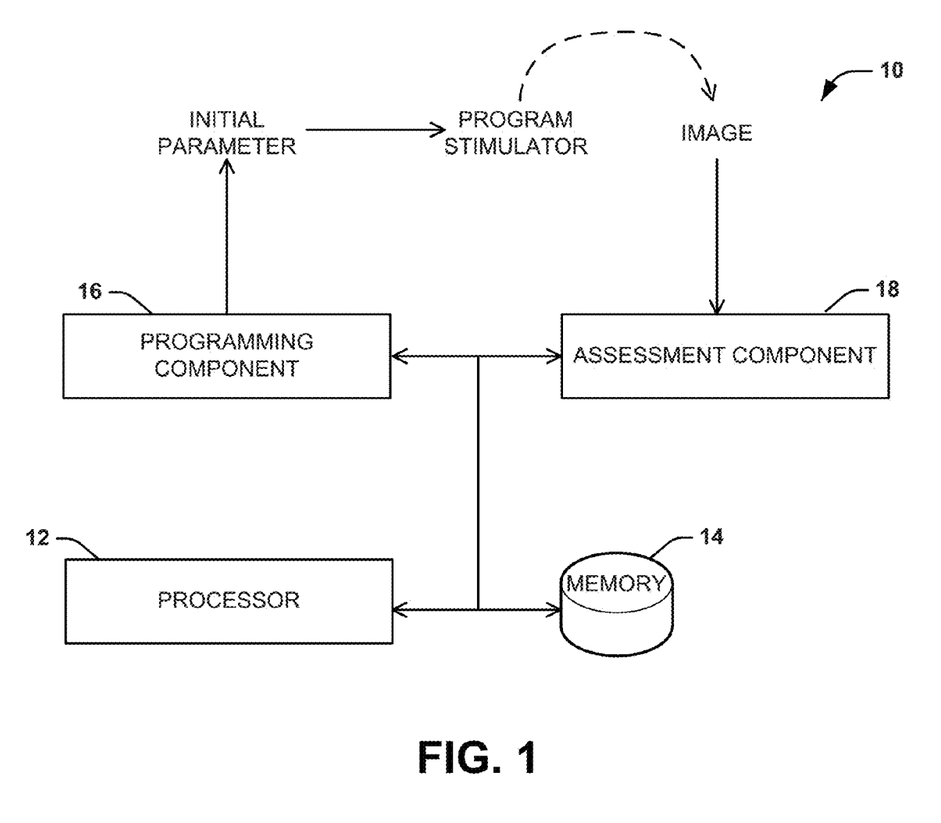
FIG. 1 is a block diagram of an example system that can determine the efficacy of at least one stimulation parameter, according to an aspect of the present disclosure.

An example of a system 10, as illustrated in FIG. 1, that can that can determine the efficacy of at least one effective stimulation parameter that can be programmed into a stimulator device for a stimulation application. The system 10 can include a memory 14 storing computer-executable instructions for implementing the systems and a processor 12 to access the memory and execute the computer-executable instructions to perform operations of the system 10. The operations of the system 10 can include the functionality of the programming component 16 and the assessment component 18.

The programming component 16 can be used to send a signal to the stimulator device to program the stimulator device according to the initial parameter. The stimulator device can apply stimulation waveforms according to the stimulation parameter. For example, stimulator devices of neural stimulation systems can utilize regular patterns of continuous stimulation with rectangular biphasic waveforms. The initial parameter can include one or more parameters of a standard waveform (e.g. amplitude, pulse width, frequency, duration, or the like) and/or properties related to the electrode contacts to apply the stimulation waveform.

In some instances, the programming component 16 can be directly connected to the stimulator device. In other instances, the programming component 16 can be indirectly (e.g., wirelessly) connected to the device. The programming component 16 can be communicatively coupled to the assessment component 18 to receive the initial parameter upon determination by the assessment component. In some instances, the stimulator can be programmed initially (e.g., upon implantation) with the initial parameter. In other instances, the stimulator can be programmed after healing from implantation surgery with the initial parameter.

The assessment component 18 can receive feedback of an image (e.g., a structural image and/or a functional image) and can determine the efficacy of the stimulation parameter based on the image. In some instances, the image can be taken during a resting state of the patient. In other instances, the image can be taken as the patient accomplishes a task. For example, the functional image can include a baseline image that can be taken before stimulation, an image with the stimulation off (STIM OFF), and/or an image with the stimulation on (STIM ON).

In some instances, the feedback can provide a detailed characterization of a patient's structural characteristics/functional activity at baseline as well as in response to the stimulation, new stimulation paradigms can be determined. For example, without being bound by theory, it is likely that the stimulation does not normalize functional activity to the pre-disease state, but instead produces atypical/abnormal brain activity that is nevertheless therapeutic. A detailed characterization of these changes and their relation to clinical outcome can suggest the need for more complex stimulation patterns or waveforms. Accordingly, the system 10 allows for the development of stimulation waveforms and paradigms that produce superior clinical outcomes with respect to current stimulation and neuromodulation systems.

Figure 2:
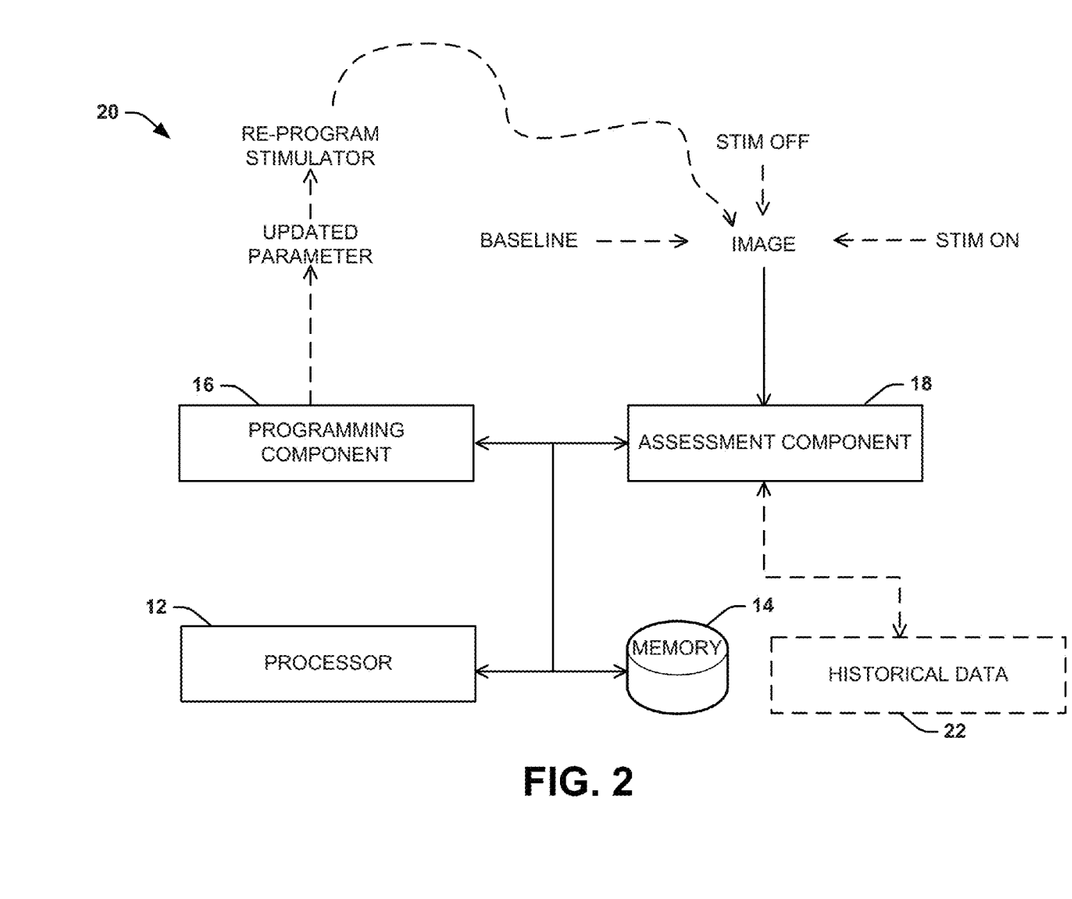
FIG. 2 is a block diagram of an example of the system in FIG. 1 updating the at least one stimulation parameter based on the determined efficacy.

As shown in FIG. 2, the assessment component 18 can use the image as feedback to change the parameter to a different updated parameter. The programming component 16 can reprogram the stimulator with the updated parameter. Unlike prior solutions, the system 20 can make these changes iteratively over a longitudinal time period. Accordingly the image can be fed into the assessment component 18, which can determine whether the results seen in the image are optimal or sub-optimal until a therapeutic setting of parameters is found. This feedback can be repeated over as many iterations as necessary until the parameter that is finally therapeutic is found. Additionally, in some instances, the feedback can be provided and the parameter updated in pseudo real time (e.g., the input data from the functional image can be processed within milliseconds to seconds so that the updated parameter is rapidly available). In other instances, stimulator programming can occur over longer periods of time that can involve multiple programming sessions.

Figure 3:
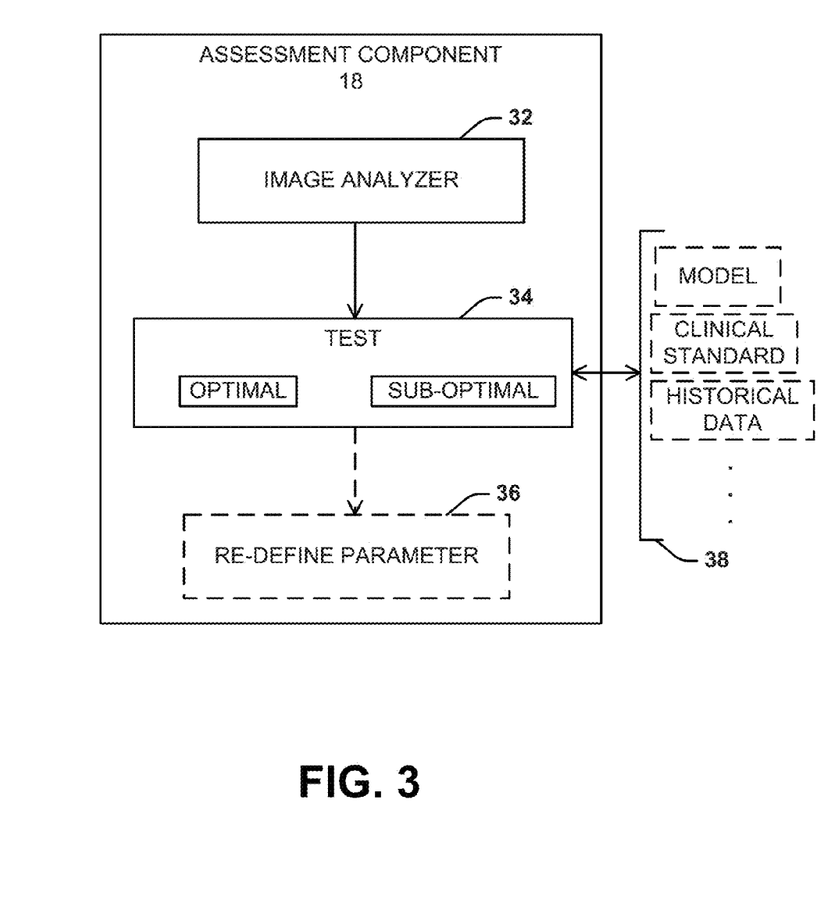
FIG. 3 is a block diagram of an example assessment component of the system of FIG. 1.

As shown in FIG. 3, the assessment component 18 can receive the image and analyze the image using an image analyzer 32. For example, the image analyzer can use historical data to determine what aspects shown in the image are the most predictive of optimal or sub-optimal stimulation. The initial stimulation parameter can be changed based on a feedback image received from an imaging modality (e.g., a structural image and/or a functional image). The image can include at least a portion of the patient after implantation of the stimulation device. The portion of the patient can include any part of the patient's body known to be affected by the stimulation.

The assessment component 18 can include a test portion 34 can be used to determine if the stimulation with the initial parameter is optimal or sub-optima and re-define the parameter 36 in conditions where the stimulus is sub-optimal. When completing the test portion, the assessment component 18 can assess the portions of the image determined by the image analyzer 32 and compare to comparators 38, such as a patient-specific model, a clinical standard, and/or historical data.

For example, the historical data can have examples of ineffective therapies/parameters and effective therapy/parameters. As another example, the historical data can include brain signatures/patterns or other physiological signatures/patterns that are indicative of an effective stimulation. In some instances, the examples can be part of population-averaged metrics of a large number of subjects with a specific disorder receiving a specific stimulation. For example, the assessment component 18 can compare parameters determined based on the image for the patient with the population-averaged metrics of a large number of subjects in the determination of therapeutic efficacy. The data related to the patient (optimal and/or sub-optimal parameters) can be added to the historical data and can be used to further aid future determinations.

In another example, the model can be a patient-specific model, a canonical model, a generalized model, or any other type of model that can be used to determine efficacy. For example, the patient-specific model can be created based on one or more imaging studies of the patient before and/or after implantation of a stimulation device (e.g., an electrode, an optode, etc.). In at least a portion of the images, the stimulation device can be visible, as well as the neighboring anatomy. The patient-specific model can take into account the anatomical features of the patient near the implantation area. A theoretically-optimal parameter can be determined based on the anatomical features. In other instances, the patient-specific model can be created based on one or more functional imaging studies. For example, the functional imaging can be accomplished before implantation, after implantation, but before stimulation programming, or after stimulation programming. In other instances, the patient specific model can be created based on a structural imaging study and a functional imaging study.

Figure 4:
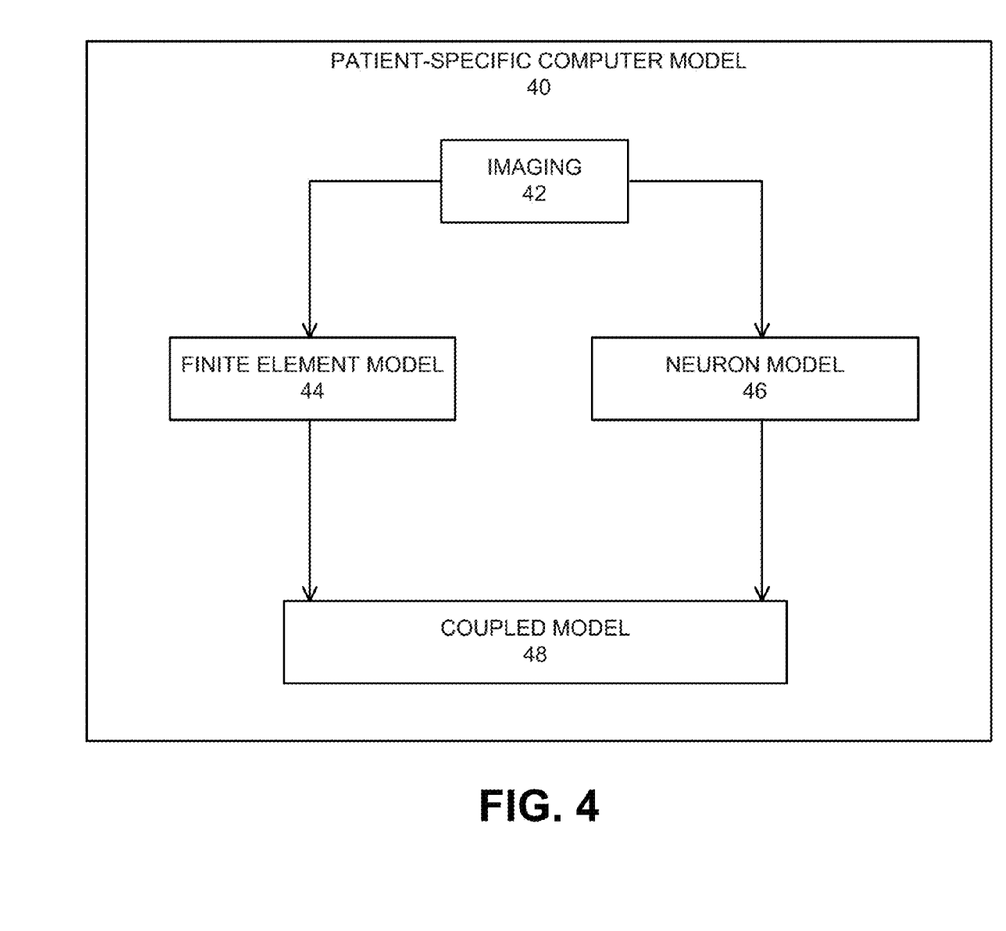
FIG. 4 is a block diagram of an example of a patient-specific computer model that can be used by the assessment component of FIG. 3.

As illustrated in FIG. 4, the patient-specific computer model 40 can include one or more sub-models. The patient-specific computer model 40 can include one or more of the sub-models illustrated, and need not include all of the sub-models illustrated. In some instances, the patient-specific model can include a neuron model 46 that includes axon trajectories (e.g., in three-dimensions). The neuron model 46 can be determined based on one or more imaging studies 42. In other instances, the patient-specific model can include a finite element model 44 that can be used to determine the areas stimulated upon the stimulation. The finite element model 44 can be determined based on one or more imaging studies 42. In still other instances, the patient-specific model can include a coupled finite element model-neuron 48 model that can illustrate the axons stimulated with a particular contact configuration. The axons stimulated can also depend on the stimulation pattern delivered by a particular contact configuration (e.g., configuration of electrodes, optodes, or the like that can deliver the stimulus). Each of the sub-models individually or in combination can be used to determine the theoretically-ideal stimulus parameter. The imaging studies 42, in some instances, can include functional images sent as feedback, which can be used so that the patient-specific computer model 40 can be used to determine a new stimulation parameter.

Figure 5:
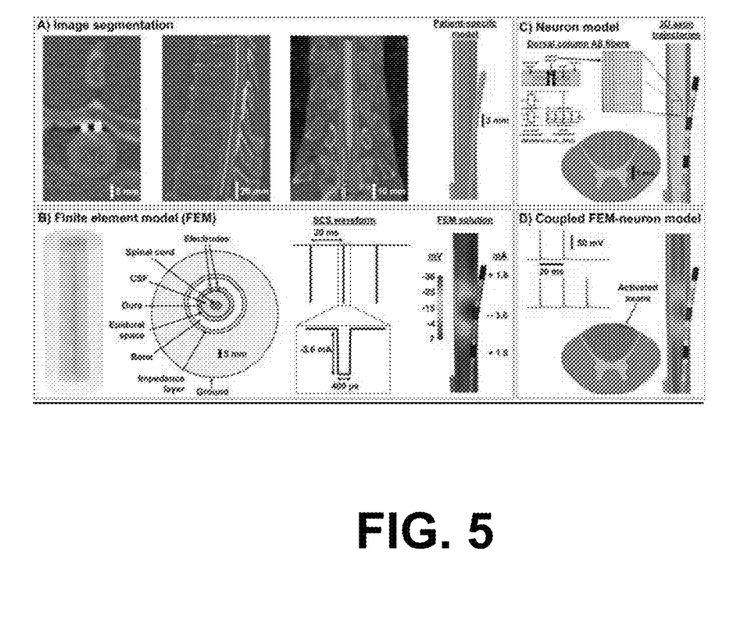
FIG. 5 shows a particular example of the patient-specific computer model of FIG. 4 with relation to spinal cord stimulation.

A particular example of the patient-specific computer model with relation to spinal cord stimulation with electrodes is shown in FIG. 5. An image can be taken of the portion of the patient with the implanted electrodes. In FIG. 5(A), image segmentation is performed to determine a patient-specific anatomy and electrode locations. In FIG. 5(B), a finite element model (FEM) is generated from the image segmentations and a voltage distribution is calculated for the desired stimulus parameter. In FIG. 5(C), multi-compartment neural models are placed within the appropriate patient anatomy. In FIG. 5(D), the FEM voltage distribution is coupled to the neural elements to estimate their response to SCS.

IV. Methods

Figure 6:
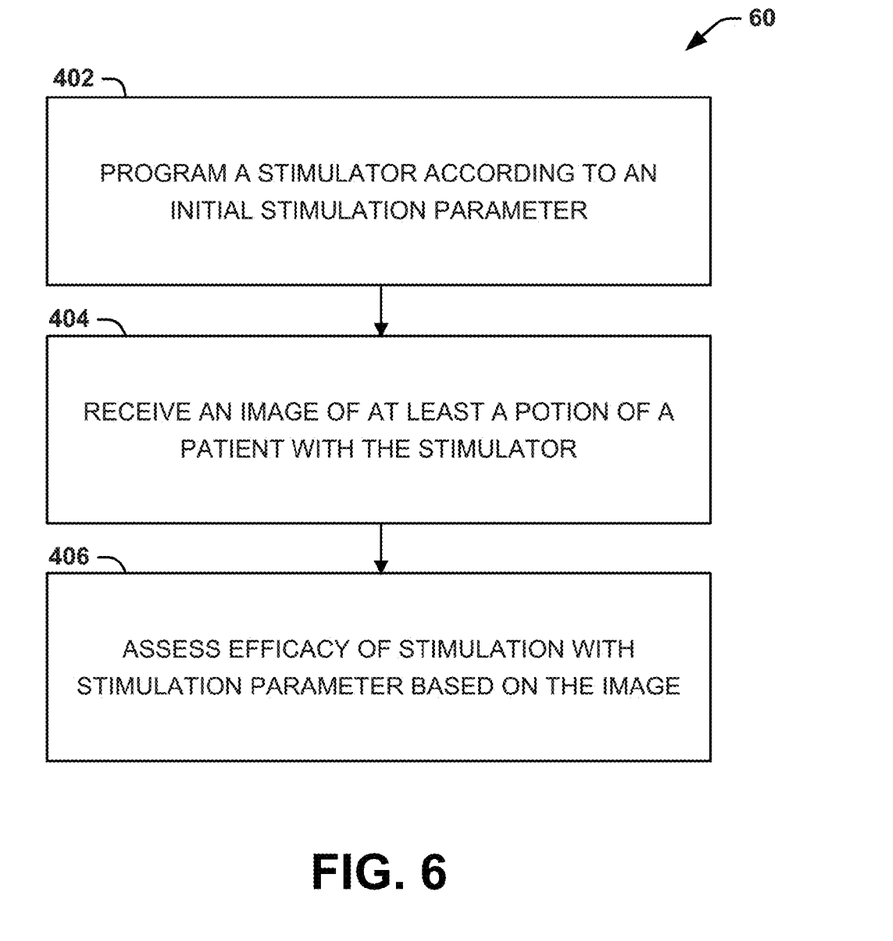
FIG. 6 is a process flow diagram of a method for determining the efficacy of at least stimulation parameter, according to another aspect of the present disclosure.
Figure 7:
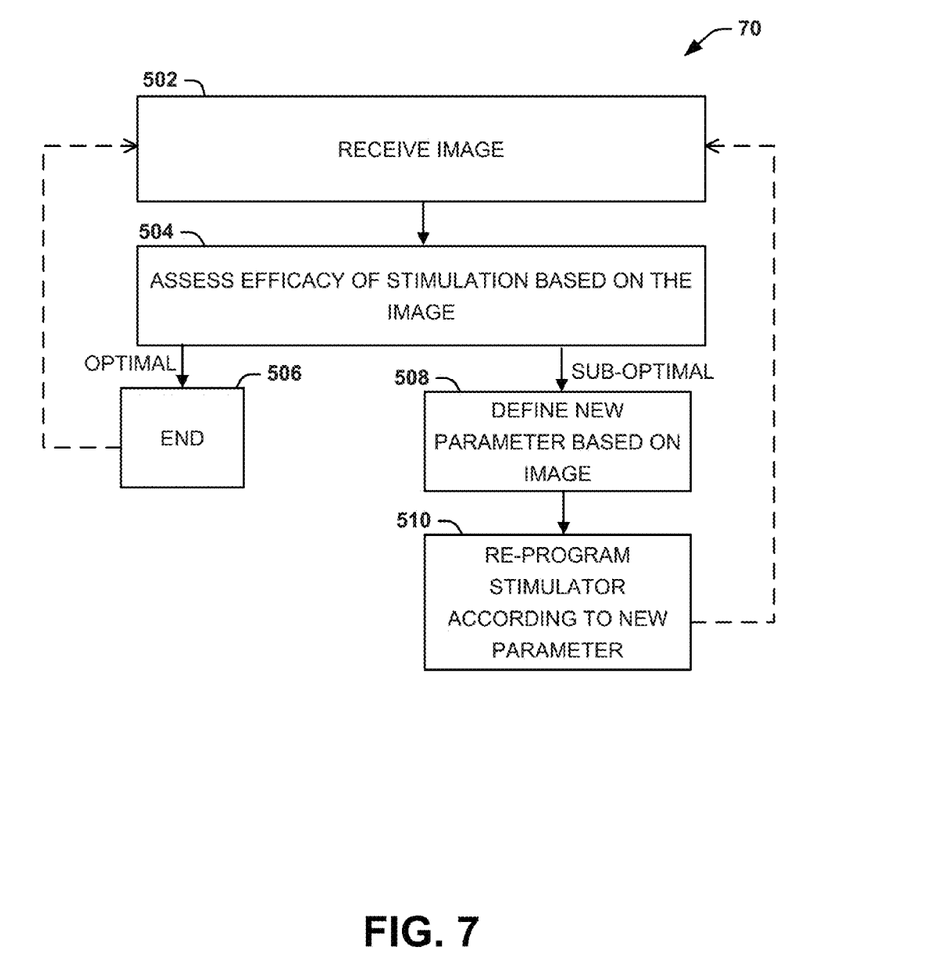
FIG. 7 is a process flow diagram of a method for updating the at least one stimulation parameter of FIG. 6 based on the efficacy.
Figure 8:
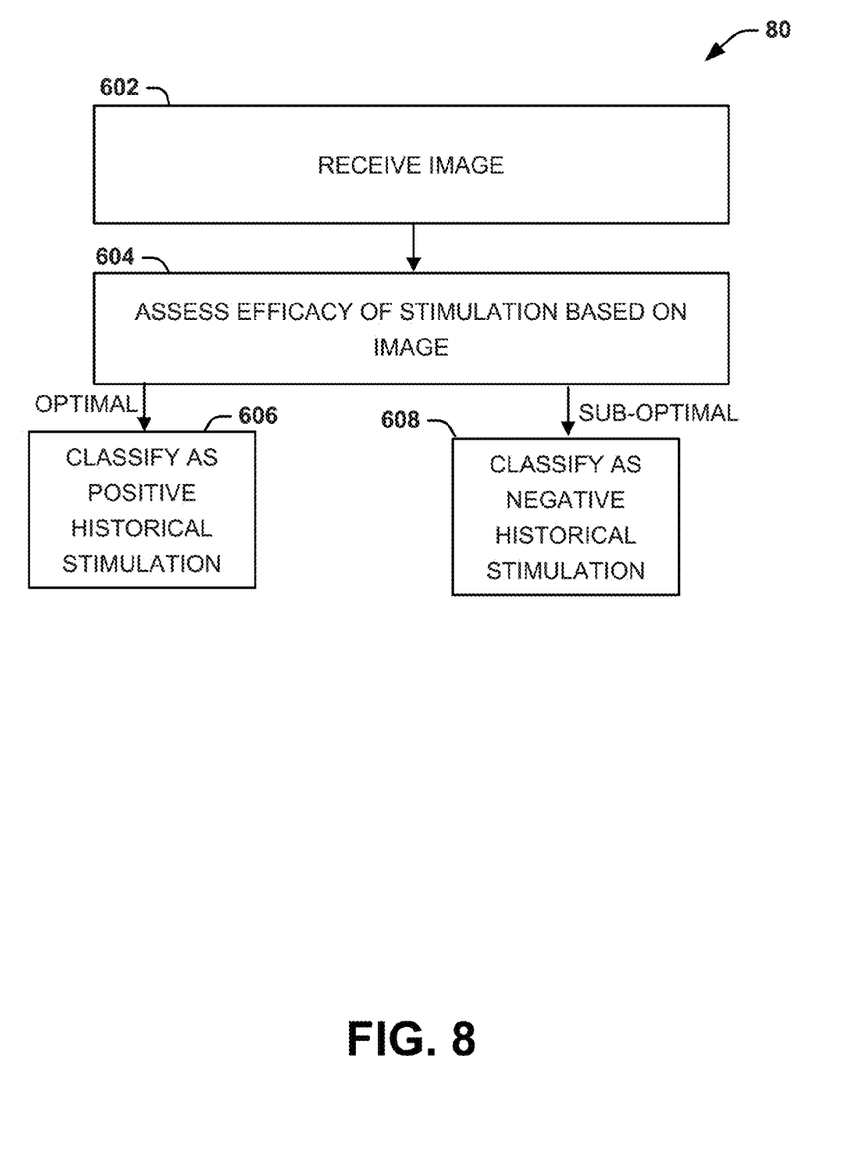
FIG. 8 is a process flow diagram of a method for updating historical data that can be used to determine the efficacy of the at least one stimulation parameter of FIG. 6.

Another aspect of the present disclosure can include methods for determining at least one effective stimulation parameter based on a patient-specific computer model and functional imaging. FIG. 6 illustrates a method 60 for determining the efficacy of at least one stimulation parameter. FIG. 7 illustrates a method 70 for updating the at least one stimulation parameter of FIG. 6. FIG. 8 illustrates a method 60 for updating historical data that can be used to determine the at least one stimulation parameter of FIG. 6.

The methods 60-80 are illustrated as a process flow diagram with flowchart illustrations. For purposes of simplicity, the methods 60-80 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 60-80.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 60-80 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Referring now to FIG. 6, illustrated is a method 60 for determining at least one stimulation parameter based on a patient-specific computer model and functional imaging. At 402, a stimulator can be programmed according to an initial stimulation parameter. For example, the initial stimulation parameter can be determined before the first stimulation and/or after feedback is received. In some instances, the initial stimulation parameter can be determined using a patient-specific model or other type of model, like a general model or a canonical model. In other instances, the initial stimulation parameter can be determined based on the most efficacious parameters determined with standard clinical programming methods.

At 404, an image can be received of at least a portion of the patient after the stimulator is set with the parameter is received. In some instances, the image can be a structural image. In other instances, the image can be a functional image. In still other instances, the image can include a structural image and a functional image. The image can be fed back to facilitate assessment of the stimulation. At 406, the efficacy of the stimulation with the stimulation parameter can be assessed based on the functional image. In some instances, the method 60 can be performed as a loop until therapeutic parameters are found.

An example method 70 executing this loop is shown in FIG. 5. At 502, an image (e.g., a structural and/or functional image) can be received, and at 504, the efficacy of the stimulation can be assessed based on the image. The assessment can be categorized as "optimal" or "sub-optimal"

corresponding to whether a therapeutic effect was seen or not. If the stimulation is categorized as "optimal", the method ends at 506. However, another image can still be received to start the method 70 over again.

If the stimulation is categorized as "sub-optimal", steps 508-510 can be undertaken. At 508, a new parameter can be defined based on the image. The feedback image can be used as an input to the assessment component that can determine the new parameter. At 510, the stimulator can be re-programmed according to the new parameter. The feedback process can begin again with another image being received to start the method 70 over again.

In some instances, as shown in the method 80 of FIG. 8, the results of the efficacy assessment can be stored for future use (e.g., in future assessments of the patient and/or another patient). Steps 602 and 604 are similar to steps 502 and 504 of FIG. 5. Namely, a functional image is received at 602 and the efficacy of the stimulation is assessed based on the functional image at 604. At 606, if the assessment classifies the stimulation as optimal, it (and its parameter) can be classified (e.g., in historical data) as a positive historical stimulation. Analogously, at 608, if the assessment classifies the stimulation as sub-optimal, it (and its parameter) can be classified (e.g., in historical data) as a negative historical stimulation. In some instances, the image can also be stored with the assessment.

V. Example

The example described below refers to a patient suffering from a medical condition and deemed a candidate for therapy. A medical condition can be any medical disorder, dysfunction, or disease and "treating" a medical condition includes improving the medical condition, suppressing the medical condition, alleviating symptoms of the medical conditions, or any combination thereof. As stated above, the stimulation can be used to treat a variety of medical conditions, including, for example, stroke recovery; deficits from multiple sclerosis; Parkinson's disease and other movement disorders; chronic pain; depression anxiety and other psychiatric disorders; and neurodegenerative disorders. In a preferred embodiment, the present invention is directed to determining effective stimulation parameters using resting state fMRI to treat chronic pain by SCS.

As described above, the effective stimulation parameters can be used in a stimulation that is applied to a patient to improve a patient's medical condition. A patient is first identified as a candidate for neurostimulation. An initial set of parameters is determined by a patient-specific model. The patient receives therapeutic intervention with an initial set of parameters. Functional measurements, such as fMRI, for example, are performed to serve as feedback that can be used to determine whether the patient's brain patterns are consistent with target brain patterns that have been associated with good outcomes. If not, the therapy parameters are adjusted and the functional measurements are performed again. Once the patient's brain patterns are sufficiently consistent with the target brain patterns that are representative of effective therapy, the stimulation parameters are considered effective to treat the medical condition.

Figure 9:
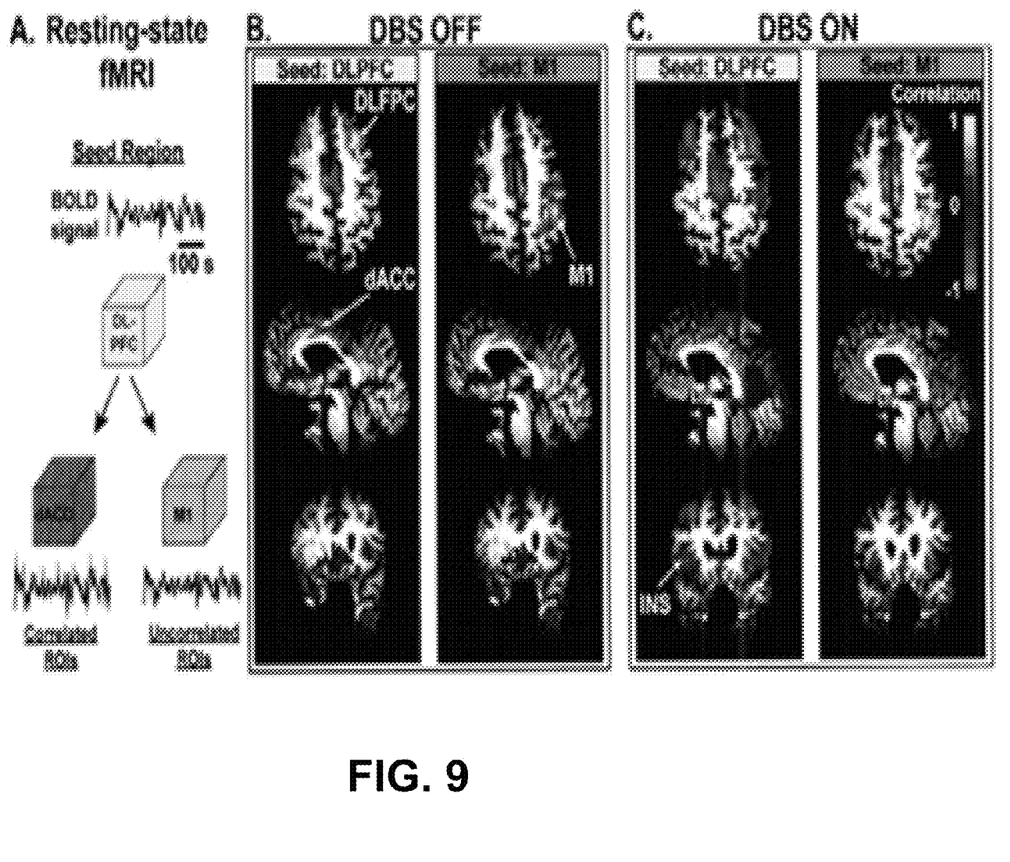
FIG. 9 demonstrates an example of functional measurements of a patient's brain patterns that can be used to determine the at least one effective stimulation parameter.

FIG. 9 demonstrates an example of functional measurements of a patient's brain patterns that can be used to determine the at least one effective stimulation parameter. In this example, a patient's brain patterns are characterized with resting-state functional magnetic resonance imaging (fMRI) using a seed-based analysis. FIG. 9A is a schematic outline that demonstrates, in this example, that resting state fMRI examines synchrony between a seed region and the remaining brain voxels in the low-frequency blood oxygen level dependent (BOLD) signal. Therefore, FIG. 9B and FIG. 9C illustrate voxels of a resting state fMRI image with time-domain BOLD signals that are either positively or negatively correlated with the time-domain BOLD signal of the seed region (dorsolateral prefrontal cortex (DLPFC) or motor cortex (M1) in this example). FIG. 9B is a resting state fMRI image with the DBS system turned off. With "DBS OFF," the patient exhibited moderate connectivity between the DLPFC and the dorsal anterior cingulated cortex (dACC). FIG. 9C is a resting state fMRI image with the DBS system turned on. During chronic DBS, the patient exhibited enhanced connectivity between the DLPFC and dACC as well as significant connectivity between the DLPFC and insular cortex (INS). M1 did not demonstrate connectivity with these pain networks in either situation.

Figure 10:
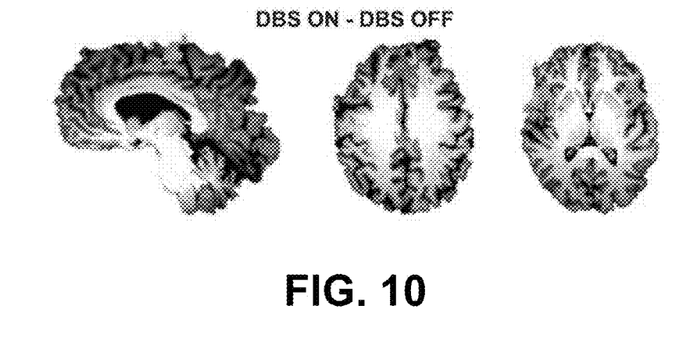
FIGS. 10 and 11 demonstrate example functional images showing task-state (FIG. 10) and resting-stage (FIG. 11) results.

FIG. 10 demonstrates an example of task-state fMRI measurements performed in a patient that experienced significant clinical improvements in response to deep brain stimulation (DBS) in the ventral capsule and ventral striatal area (VC/VS) for refractory intractable hemibody pain. During the imaging a painful heat stimulus was applied to one of the patient's wrists. Task-state imaging sessions were performed after approximately two months with the DBS system turned ON and after approximately two months with the DBS system turned OFF. For each imaging session, the brain areas demonstrating statistically significant responses to the stimulus were determined from changes in the BOLD signal. FIG. 10 shows statistically significant activation differences between the DBS ON and the DBS OFF conditions (i.e. DBS ON-DBS OFF). During therapeutically effective stimulation certain areas of the patient's brain displayed increased activation and deactivation in response to the painful heat stimulus. These activation differences suggest modified processing of acute pain during clinically effective stimulation.

Figure 11:
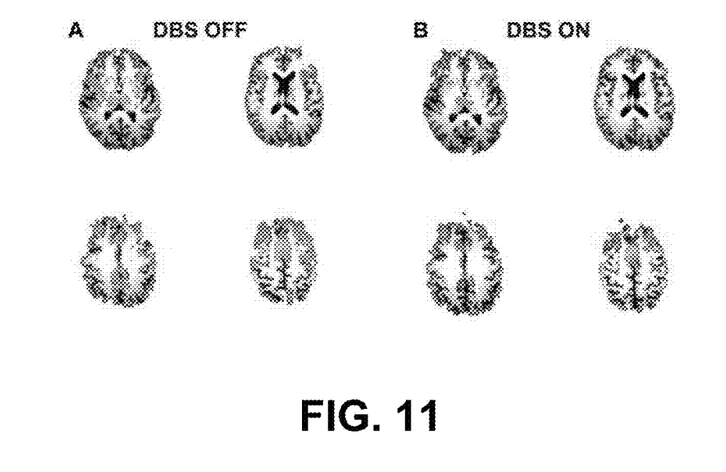

FIG. 11 demonstrates resting-state fMRI measurements performed in a patient that experienced significant clinical improvements in response to VC/VS DBS. Axial views of the fMRI measurements with DBS OFF and DBS ON are shown in parts A and B, respectively. With the DBS turned OFF, the patient demonstrate significant functional connectivity between the midcingulate cortex and other pain areas known to be involved in chronic pain processing (e.g. anterior insular cortex, dorsolateral prefrontal cortex). With the DBS turned ON, the functional connectivity between the midcingulate cortex and these other pain processing centers is significantly reduced. This example demonstrates the ability to detect the modulation of brain activity in response to clinically effective stimulation.

From the above description, those skilled in the art will perceive improvements, changes and modifications. Such improvements, changes and modifications are within the skill of one in the art and are intended to be covered by the appended claims.

What is claimed is:
1. A method comprising:
programming a stimulation device with at least one initial stimulation parameter, wherein the at least one initial stimulation parameter is determined using a patient-specific computer model of a portion of the patient's body affected by a stimulation by the stimulation device;
receiving, by a system comprising a processor, a functional image of the portion of the patient's body after implantation of the stimulation device during the stimulation by the stimulation device with the initial stimulation parameter; and assessing, by the system, an efficacy of the stimulation with the at least one initial stimulation parameter based on the functional image, wherein the assessing comprises evaluating a therapeutic effect of the stimulation; and adjusting, by the system, the at least one initial stimulation parameter based on the assessment.

2. The method of claim 1, wherein the patient-specific computer model comprises at least one of a finite element model, a neuron model, and a coupled model.

3. The method of claim 1, further comprising re-programming the stimulation device implanted in the patient with the adjusted at least one stimulation parameter.

4. The method of claim 3, further comprising:
receiving another image of the at least the portion of the patient affected by the stimulation; and
re-assessing the efficacy of the stimulation with the re-defined at least one stimulation parameter based on the another image.

5. The method of claim 1, wherein the functional image is acquired by at least one of functional magnetic resonance imaging (fMRI), evoked potentials, local field potential (LFP), electrocorticography (ECoG), electroencephalography (EEG), magnetoencephalography (MEG), electromyography (EMG), positron emission tomography (PET), magnetic resonance spectroscopy (MRS), optical tomography (OT), computed tomography (CT), single-photon emission computed tomography (SPECT), ultrasound, laser Doppler measurements, and near-infrared (NIR) spectroscopy.

6. The method of claim 1, wherein the functional image is obtained during at least one of a resting state of the patient and a task state of the patient.

7. The method of claim 1, wherein the stimulation is at least one of spinal cord stimulation, deep brain stimulation, cortical stimulation, peripheral nerve stimulation, cranial nerve stimulation, muscular stimulation, and cardiac stimulation.

8. The method of claim 1, wherein the efficacy of the stimulation is assessed based on a metric determined based on historical data from a population of subjects suffering from the same medical condition as the patient.

9. The method of claim 8, further comprising updating the metric based on the assessed efficacy of the stimulation with the at least one theoretically optimal stimulation parameter.

10. The method of claim 1, wherein the at least one initial stimulation parameter comprises at least one of amplitude, a frequency, a pulse width, and a duration.

11. The method of claim 1, wherein the at least one initial stimulation parameter comprises a selection of at least one electrode to deliver the stimulation and a polarity of the selected at least one electrode.

12. A system comprising:
a memory storing computer-executable instructions; and
a processor to access the memory and execute the computer-executable instructions to at least:
program a stimulation device with an initial stimulation parameter, wherein the initial stimulation parameter is determined using a patient-specific computer model of a portion of the patient's body affected by a stimulation by the stimulation device;
receive a functional image of the portion of the patient's body after implantation of the stimulation device during the stimulation by the stimulation device with the initial stimulation parameter;
assess an efficacy of the stimulation with the initial stimulation parameter based on the functional image, wherein the assessment evaluates a therapeutic effect of the stimulation; and
adjust the initial stimulation parameter based on the assessment.

13. The system of claim 12, wherein the patient-specific computer model comprises at least one of a finite element model, a neuron model, and a coupled model.

14. The system of claim 12, wherein the processor executes the computer-executable instructions to re-program the stimulation device implanted into the patient with the adjusted stimulation parameter.

15. The system of claim 14, wherein the processor executes the computer-executable instructions to:
receive another image of the at least the portion of the portion of the patient's body; and
assess the efficacy of the stimulation with the adjusted stimulation parameter based on the another image.

16. The system of claim 12, wherein the functional image is acquired by at least one of functional magnetic resonance imaging (fMRI), evoked potentials, local field potential (LFP), electrocorticography (ECG), electroencephalography (EEG), magnetoencephalography (MEG), electromyography (EMG), positron emission tomography (PET), magnetic resonance spectroscopy (MRS), optical tomography (OT), computed tomography (CT), single-photon emission computed tomography (SPECT), ultrasound, laser Doppler measurements, and near-infrared (NIR) spectroscopy.

17. The system of claim 12, wherein the stimulation is at least one of spinal cord stimulation, deep brain stimulation, cortical stimulation, peripheral nerve stimulation, cranial nerve stimulation, muscular stimulation, and cardiac stimulation.

18. The system of claim 12, wherein the processor further executes the computer-executable instructions to optimize a stimulation waveform based on the assessed efficacy by adjusting the initial stimulation parameter.

19. The system of claim 12, wherein the functional image is obtained during at least one of a resting state of the patient and a task state of the patient.

* * * * *